United States Patent
O'Malley et al.

(10) Patent No.: US 9,157,079 B2
(45) Date of Patent: Oct. 13, 2015

(54) SOLID MATRIX FOR THE STORAGE OF BIOLOGICAL SAMPLES

(71) Applicant: GE HEALTHCARE UK LIMITED, Little Chalfont (GB)

(72) Inventors: Hugh O'Malley, Maidstone (GB); Barry Johnson, Maidstone (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 0 days.

(21) Appl. No.: 13/832,139

(22) Filed: Mar. 15, 2013

(65) Prior Publication Data

US 2014/0272983 A1 Sep. 18, 2014

(51) Int. Cl.
  *C07H 21/00* (2006.01)
  *C12N 15/10* (2006.01)

(52) U.S. Cl.
  CPC ............ *C12N 15/1006* (2013.01); *C07H 21/00* (2013.01); *C12N 15/1017* (2013.01)

(58) Field of Classification Search
  CPC ...................................... C07H 21/00
  USPC ......................................................... 536/25.4
  See application file for complete search history.

(56) References Cited

U.S. PATENT DOCUMENTS

| | | | |
|---|---|---|---|
| 5,939,259 A | 8/1999 | Harvey et al. | |
| 2011/0054157 A1 | 3/2011 | Bitner | |
| 2014/0154667 A1* | 6/2014 | Lamerton et al. | 435/5 |
| 2014/0154693 A1* | 6/2014 | Porschewski | 435/6.12 |

OTHER PUBLICATIONS

Sigma Chemical Company 1995 Catalog, (4 sheets).*
Jul. 9, 2014 Written Opinion of the International Searching Authority Issued in International Application No. PCT/EP2014/055038.

* cited by examiner

*Primary Examiner* — Ardin Marschel
(74) *Attorney, Agent, or Firm* — Sutherland Asbill & Brennan LLP

(57) ABSTRACT

The present invention relates to a method for storage and subsequent lysis of a sample in which the sample is immobilized on a solid support. The solid matrix is embedded with a low concentration of both a chaotropic salt and a surfactant which act synergistically to efficiently store and lyse a biological sample.

12 Claims, 1 Drawing Sheet

SOLID MATRIX FOR THE STORAGE OF BIOLOGICAL SAMPLES

FIELD OF INVENTION

The present invention relates to the field of sample collection for nucleic acid amplification, particularly to the use of the polymerase chain reaction to amplify nucleic acids. The invention provides methods and kits which can be used to collect cell samples containing nucleic acids by reducing the use of chemicals that may interfere with the polymerase chain reaction. The invention has applications in the long-term storage, recovery and further processing of nucleic acids and is particularly useful in genotyping, diagnostics and forensics applications.

BACKGROUND OF THE INVENTION

Long-term storage, transport and archiving of nucleic acids on filter paper or chemically modified matrices is a well-known technique for preserving genetic material before the DNA or RNA is extracted and isolated in a form for use in genetic analysis such as PCR. Thus, EP 1563091 (Smith et al, Whatman) relates to methods for storing nucleic acids from samples such as cells or cell lysates. The nucleic acid is isolated and stored for extended periods of time, at room temperature and humidity, on a wide variety of filters and other types of solid support or solid phase media. Moreover, the document describes methods for storing nucleic acid-containing samples on a wide range of solid support matrices in tubes, columns, or multiwell plates.

WO 90/03959 (Burgoyne) describes a cellulose-based solid support for the storage of DNA, including blood DNA, comprising a solid matrix having a compound or composition which protects against degradation of DNA incorporated into or absorbed on the matrix. This document also discloses methods for storage of DNA using the solid medium, and for recovery of or in situ use of DNA.

U.S. Pat. No. 5,705,345 (Lundin et al.) describes a method of nucleic acid preparation whereby the sample containing cells is lysed to release nucleic acid and the sample is treated with cyclodextrin to neutralize the extractant. The advantage of this system is that conventional detergent removal requires a separation step however with the addition of cyclodextrin to neutralize the detergent it would remove the separation step needed and reduce chance of contamination.

U.S. Pat. No. 5,496,562 (Burgoyne) describes a cellulose-based solid medium and method for DNA storage. Method for storage and transport of DNA on the solid medium, as well as methods which involve either (a) the recovery of the DNA from the solid medium or (b) the use of the DNA in situ on the solid medium (for example, DNA sequence amplification by PCR) are disclosed. The method described incorporates a surfactant or detergent on the surface of the solid medium and would require a separate step for the removal of the detergent before PCR is performed as a detergent would interfere with the PCR process.

EP 2290099 B1 (Qiagen) describes again a method for processing and amplifying DNA. The method includes the steps of contacting the sample containing DNA to a solid support wherein a lysis reagent is bound to the solid support. The DNA is subsequently treated with a DNA purifying reagent and is purified.

WO96/39813 (Burgoyne) describes a solid medium for storing a sample of genetic material and subsequent analysis; the solid medium comprising a protein denaturing agent and a chelating agent. The method described is for chelating agents which are any compound capable of complexing multivalent ions including Group II and Group III multivalent metal ions and transition metal ions.

WO 96/18731 (Deggerdal) describes a method of isolating nucleic acid whereby the sample is bound to a solid support and the sample is contacted with a detergent and subsequent steps performed to isolate the nucleic acid.

WO 00/53807 (Smith, Whatman) describes a medium for the storage and lysis of samples containing genetic material which can be eluted and analyzed. The medium is coated with a lysis reagent. In addition the medium could be coated with a weak base, a chelating agent, a surfactant and optionally uric acid.

WO 99/38962 (Health, Gentra Systems Inc.) describes a solid support with a bound lysis reagent. The lysis reagent can comprise of a detergent, a chelating agent, water and optionally an RNA digesting enzyme. The solid support again would require further steps for purification of the nucleic acid for amplification analysis.

Inhibitors of PCR

There are significant problems with inhibitory substances or inhibitors interfering with polymerase chain reactions on nucleic acids, including nucleic acids stored or immobilized on solid supports such as cellulose-derived filters. Sources of inhibitors can be the materials and reagents such as detergents that come into contact with samples during processing or nucleic acid purification. These include excess KCl, NaCl and other salts, ionic detergents such as sodium deoxycholate, sarkosyl and sodium dodecyl sulphate (SDS), ethanol and isopropanol, phenol (see Burgoyne WO 90/03959) and others. All users of PCR are likely to be impacted by inhibitors at some time, but the wide range of forensic sample types and variety of sampling conditions encountered make forensic scientists particularly vulnerable.

The presence of chemicals that interfere with PCR analysis in samples is well-known and a number of approaches are documented that describe their removal. However, none of these approaches are particularly efficient. In particular the application of samples to solid supports, particularly cellulose-derived materials, increases the problems with PCR inhibition because of the inclusion of potent chemicals such as SDS and chaotropic salts which are typically used to stabilize nucleic acids on the solid support (see Burgoyne WO 90/03959).

PCR inhibitors usually affect PCR through interaction with DNA or interference with the DNA polymerase. In a multiplex PCR reaction, it is possible for the different sequences to experience different inhibition effects to varying degrees, leading to a disparity in results. Alternatively, various inhibitors reduce the availability of cofactors (such as magnesium) or otherwise interfere with the interaction of PCR cofactors with the DNA polymerase. Some of the pitfalls of quantitative real-time reverse transcription polymerase chain reaction, including the effect of inhibitors, are described by Bustin & Nolan (J. Biomolecular Techniques, 2004, 15, 155-166).

Current methods for inhibitor removal are often carried out during the DNA purification procedure by binding to single or double stranded DNA covalently linked to a support. However, this is a tedious process and prior art methods have a number of clear disadvantages in terms of cost, complexity and in particular, user time.

U.S. Pat. No. 5,705,345 (Lundin et al.) describes a method of nucleic acid preparation whereby the sample containing cells is lysed to release nucleic acid and the sample is treated with cyclodextrin to neutralize the extractant. The advantage of this system is that conventional detergent removal requires a separation step however with the addition of sequestrants such as cyclodextrin to neutralize the detergent it would remove the separation step needed and reduce chance of contamination.

WO 2010/066908 (Beckers et al.,) describes the use of cyclodextrins to improve the specificity, sensitivity and/or yield of PCR. The method claimed is an amplification reaction which is performed in a reaction mixture comprising at least one cyclodextrin and performing the amplification reaction on said reaction.

Alternative methods involve the binding of nucleic acids in the presence of chaotropic agents such that DNA binds to silica or glass particles or glass beads. This property was used to purify nucleic acid using glass powder or silica beads under alkaline conditions. Typical chaotropic agents include guanidinium thiocyanate or guanidinium hydrochloride and recently glass beads have been substituted with glass containing minicolumns. While the chaotropic agent may neutralize the interference of the detergent on the PCR process, the chaotropic agent itself may reduce the efficiency of PCR amplification.

Wang et al. (Enzyme Microbiology Technology, 1990) describes a method of recovering protein from a bacteria by exposing *E. coli* to certain combinations of guanidine and Triton X-100 in a solution. It was noted that neither of the chemicals alone and at low concentrations extracts more than 10% of intracellular protein however together were able to release over 50% overall protein.

U.S. Pat. No. 5,939,259 (Schleicher & Schuell Inc.) describes a method for the collection and storage of nucleic acids by coating an absorbent material with a solution containing from 0.5M to 2.0M chaotropic salt and allowed to dry. Other ingredients can be added to the invention in order to enhance lysis or disruption of intact cells, bacteria and viruses which include anionic, cationic or zwitterionic surfactants, such as Tween 20 or Triton X-100.

Given the wide range of PCR inhibitor-laden sample types and the options available for handling them, a multifaceted approach is the best solution for amplification failure. There is a need to reduce any potential PCR inhibitors used in the nucleic acid collection process wherein the nucleic acid is immobilized on a solid support and thereby improve PCR amplification.

The present invention addresses this problem and provides methods and kits which can be used for the collection of nucleic acids using solid supports, particularly cellulose-derived supports.

DETAILED DESCRIPTION OF THE INVENTION

Figure 1:
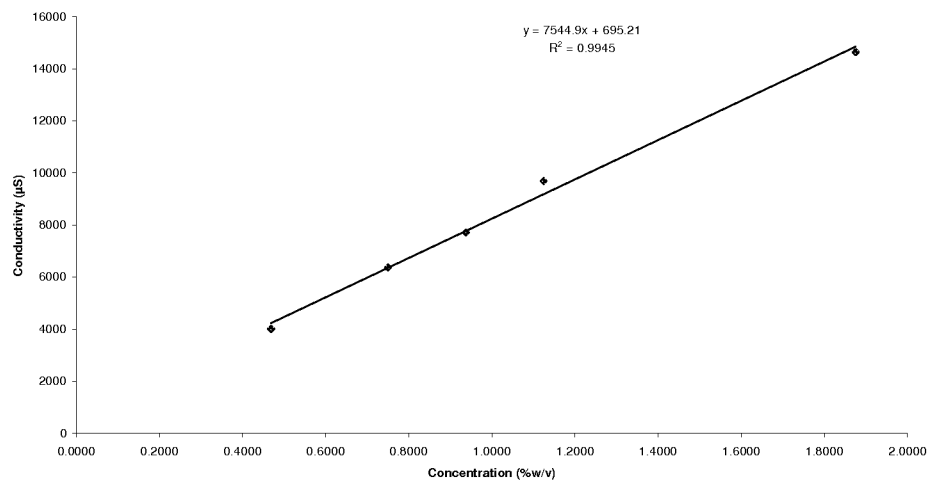
FIG. 1 shows the conductivity versus concentration of the guanidine thiocyanate treated ETF paper.

The present invention provides a solid matrix which can be used to store and lyse biological samples by contacting a solid support embedded with a surfactant and a chaotropic salt.

According to a first aspect of the present invention, there is provided a solid matrix for storing and/or lysing a biological sample comprising a surfactant and a chaotropic salt, wherein the concentration of the chaotropic salt is less than 0.5M.

The advantage of embedding a surfactant and a chaotropic salt onto a solid matrix for sample collection is the two chemicals can react synergistically to lyse the cell thereby allowing the use of a lower concentration of both chemicals. The benefits of using a lower concentration of surfactant and a chaotropic salt on a solid matrix is to reduce interference of these two chemicals in the PCR process.

In one aspect, the solid matrix wherein the chaotropic salt concentration is greater than 0.05M.

In another aspect, the solid matrix wherein the surfactant concentration is greater than 0.05M.

In a further aspect, the solid matrix wherein the surfactant concentration is less than 0.5M.

In a further aspect, the solid matrix wherein the chaotropic salt and surfactant is present in a ratio of 1:1.

In another aspect the solid matrix wherein the chaotropic salt and surfactant is present in a ratio of 1:10.

In another aspect, the solid matrix wherein the chaotropic salt and surfactant is present in a ratio of 10:1.

In a further aspect, the solid matrix wherein the concentration of chaotropic salt to surfactant is selected from the group consisting of 0.01M:01M, 0.1M:0.01M, 0.05M:0.05M, 0.1M:0.1M, 0.2M:0.2M, 0.3M:0.3M and 0.4M:0.4M.

In a further aspect the solid matrix wherein said surfactant is Triton X100.

In a further aspect the solid matrix wherein the chaotropic salt is a guanidinium salt.

In one aspect, the solid matrix wherein the chaotropic salt is selected from the group consisting of guanidine hydrochloride, guanidine isothiocyanate and guanidine thiocyanate.

In a further aspect, the solid matrix wherein the chaotropic salt is guanidine thiocyanate.

In another aspect, the solid matrix wherein the biological sample is selected from the group consisting of a cellular sample, blood, serum, semen, cerebral spinal fluid, synovial fluid, lymphatic fluid, saliva, buccal, cervical cell, vaginal cell, urine, faeces, hair, skin and muscle.

In another aspect, the solid matrix wherein the solid matrix is selected from the group consisting of: alginate, glass, glass fiber, glass microfiber, silica, silica gel, silica oxide, cellulose, nitrocellulose, carboxymethylcellulose, polyester, polyamide, carbohydrate polymers, polypropylene, polytetrafluorethylene, polyvinylidinefluoride, wool and porous ceramics.

In another aspect, the solid matrix wherein the solid matrix is a cellulose based matrix.

In another aspect, the solid matrix wherein said cellulose based matrix is in the form of a pre punched disc.

In a further aspect the solid matrix additionally wherein said cellulose based matrix is in the form of an FTA pre punched disc.

The solid matrix may comprise a glass or silica-based solid phase medium, a plastics-based solid phase medium or a cellulose-based solid phase medium. The solid support is preferably a cellulose-based matrix. Examples of cellulose-based matrices include FTA™ (data file 51668), 903 neonatal cards and 31-ETF cards available from GE Healthcare.

In a further aspect, said solid matrix is impregnated with sodium dodecyl sulfate (SDS), ethylenediaminetetracetic acid (EDTA) and uric acid.

According to a second aspect of the present invention, there is provided a method of storing and/or lysing a biological sample comprising the steps;
i) contacting a solid matrix of any preceding claim with a biological sample,
ii) storing said solid matrix with said biological sample, wherein the chaotropic salt and surfactant have a synergistic effect in lysing the cell.

In a further aspect, the method wherein the method comprises a further step iii) of recovering the cell lysate from the solid matrix.

In another aspect, the method wherein the biological sample is selected from a group comprising consisting of a cellular sample, blood, serum, semen, cerebral spinal fluid, synovial fluid, lymphatic fluid, saliva, buccal, cervical cell, vaginal cell, urine, faeces, hair, skin and muscle. The biological sample may originate from a mammal, bird, fish or plant or a cell culture thereof. Preferably the biological sample is mammalian in origin, most preferably human in origin. The sample containing the nucleic acid may be derived from any source. This includes, for example, physiological/pathological body fluids (e.g. secretions, excretions, exudates) or cell suspensions of humans and animals; physiological/pathological liquids or cell suspensions of plants; liquid products, extracts or suspensions of bacteria, fungi, plasmids, viruses, prions, etc.; liquid extracts or homogenates of human or animal body tissues (e.g., bone, liver, kidney, etc.); media from DNA or RNA synthesis, mixtures of chemically or biochemically synthesized DNA or RNA; and any other source in which DNA or RNA is or can be in a liquid medium.

In one aspect, the biological sample is immobilised on the solid support for at least 24 hours. The biological sample may be immobilised on the solid support for longer periods, for example, for at least 7 days, for at least 30 days, for at least 90 days, for at least 180 days, for at least one year, and for at least 10 years. In this way the biological sample may be stored in a dried form which is suitable for subsequent analysis. Typically, samples are stored at temperatures from −200° C. to 40° C. In addition, stored samples may be optionally stored in dry or desiccated conditions or under inert atmospheres.

According to a third aspect of the present invention, there is provided a method of manufacturing a solid matrix comprising the steps,
i) dipping a solid matrix into a mixture of a surfactant and a chaotropic salt wherein the concentration of said chaotropic salt is less than 0.5M, and
ii) allowing the solid matrix to dry.

In one aspect, the method wherein the concentration of said chaotropic salt is greater than 0.05M In another aspect, the method wherein said surfactant concentration is greater than 0.05M and is less than 0.5M.

In a further aspect, the method wherein said surfactant concentration is greater than 0.05M and is less than 0.5M.

In another aspect, the method wherein the chaotropic salt and surfactant is present in a ratio selected from the group consisting of 1:1, 1:10, 10:1.

In another aspect, the method wherein the concentration of chaotropic salt to surfactant is selected from the group consisting of 0.01M:01M, 0.1M:0.01M, 0.05M:0.05M, 0.1M:0.1M, 0.2M:0.2M, 0.3M:0.3M and 0.4M:0.4M.

In a further aspect, the method wherein said surfactant is Triton X100.

In another aspect, the method wherein the chaotropic salt is selected from the group consisting of guanidine hydrochloride, guanidine isothiocyanate and guanidine thiocyanate.

In another aspect, the method wherein the solid matrix is selected from the group consisting of: alginate, glass, glass fiber, glass microfiber, silica, silica gel, silica oxide, cellulose, nitrocellulose, carboxymethylcellulose, polyester, polyamide, carbohydrate polymers, polypropylene, polytetrafluorethylene, polyvinylidinefluoride, wool or porous ceramics.

According to a fourth aspect, a kit for storing and amplifying nucleic acid comprising a solid matrix as described herein and instructions for use thereof.

Chemicals and Materials Used
A list of the chemicals and their sources is given below:
31-ETF paper was obtained from GE Healthcare UK Limited;
Guanidinium thiocyanate (Sigma-Aldrich G9277)
Triton X100 (Sigma-Aldrich T8787)
Sterile water (Sigma W4502).
Coating tray
Glass Dipping tray
Mueller-Hinton-agar plates ("ready to use" plates of mibius—P05007A contain the agar of Oxoid—CM0337)
Sterile Rotilabo—swabs (EH 12.1 of Roth)
Sterile petri plates 80 mm
7 mm Harris Uni-core punch, 1.2 mm (Sigma, Catalogue number Z708860-25ea, lot 3110);
Forceps
Positive 31-ETF control from previous lots of FTA®-treated paper
TSB (Oxoid Tryptone Soy Broth, Art-Nr. CM0129)—150 ml in Erlenmeer flask for culture suspension.
95% and 70% Ethyl alcohol
*Staphylococcus aureus* (ATCC 25923 strain)
Measuring ruler
Experimental Results
ETF paper was coated in a mixture of Guanidine Thiocyanate and Triton X100 using a hand dipping technique. Several mixtures of various molar concentrations of Guanidine Thiocyanate: Triton X100 was prepared.

An example of the preparation method used to produce the mixture of Guanidine Thiocyanate: Triton X100 was as follows:
For a 0.5M:0.5M Guanidine Thiocyanate: Triton X100 solution 32.5 g of Triton X100 was slowly added to 100 mL of $dH_2O$, using a dropping funnel, due to the low solubility of Triton X100 in water the solutions was continuously stirred as the reagent was added to the water. Once the Triton X100 had dissolved 5.908 g of Guanidine Thiocyanate was slowly added and the solution was stirred to ensure a homogenous solution. The ETF paper was dipped into the homogenous solution and allowed to dry.

Table 1 below shows the concentrations and weight of Guanidine Thiocyanate and Triton X100 used in the different sample preparations.

TABLE 1

| Thiocyanate:Triton X100 molar concentrations | Weight of Triton X100 used in grams | Weight of Guanidine Thiocyanate used in grams |
|---|---|---|
| 0.5M | 32.5 | 5.908 |
| 0.4M | 26.0 | 4.726 |
| 0.3M | 19.5 | 3.544 |
| 0.2M | 13.0 | 2.363 |
| 0.1M | 6.5 | 1.181 |
| 0.01M | 0.65 | 0.118 |

The coated ETF paper samples were measured for the zone of inhibition (ZOI). A visible zone of inhibition, described as the area encompassing the punch where bacterial growth is inhibited, is used to assess the anti-microbial action of the FTA treated paper.

A day before the ZOI test the *Staphylococcus aureus* suspension was prepared in a 150 mL simple concentrates Tryptone Soy Broth. The culture suspension flask was incubated at 37° C. after the inoculation 18±2. Three punches were taken from each individual ETF treated sample. The 7 mm punch was rinsed with 95% EtOH after each punch was taken. The punches were placed in a sterile plate. The negative control was an untreated ETF paper. A sample from a previous lot of ETF treated paper that produced a well-defined ZOI was used as the positive control.

A germ count was performed for a growth confirmation of the culture suspension. The culture suspension had a minimum of $10^8$ CFU/mL for the test to count. The culture suspension was applied on to a single agar plate with a sterile swab. For each tested sample a minimum of 3 plates were prepared. Using forceps and aseptic technique, the paper punches were placed onto the appropriate Mueller-Hinton agar plate—each plate contained a positive and a negative sample, along with 3 punches of the same sample paper. The plates were incubated in an aerobic incubator at 37° C. and were examined after 16 to 18 hours of incubation and a second time when necessary. The ZOI was calculated using a ruler to measure the diameter (including the 7 mm disc) of each zone of complete inhibition to the nearest whole millimeter. The area showing no macroscopically visible growth is defined as the end point.

The results showing the ZOI of ETF coated with varying concentrations of Guanidine Thiocyanate and Triton X100 are shown in table 2 and table 3 below.

TABLE 2

| Molar Concentration of Guanidine:Triton X100 | Bacteria free areola in mm | | |
|---|---|---|---|
| 0.5M:0.5M | 11 | 11 | 11 |
| 0.4M:0.4M | 10 | 11 | 11 |
| 0.3M:0.3M | 11 | 11 | 11 |
| 0.2M:0.2M | 11 | 11 | 11 |
| 0.1M:0.1M | 11 | 11 | 11 |
| 0.01M:0.01 | 0 | 0 | 0 |

TABLE 3

| Number | Guanidine conc M | Triton X100 conc M | Bacteria free areola in mm | | |
|---|---|---|---|---|---|
| 1 | 0.01 | 0.1 | 0 | 0 | 0 |
| 2 | 0.1 | 0.01 | 8 | 8 | 8 |
| 3 | 0.01 | 0.1 | 0 | 0 | 0 |
| 4 | 0.01 | 0.01 | 0 | 0 | 0 |
| 5 | 0.055 | 0.055 | 8 | 8 | 8 |
| 6 | 0.1 | 0.1 | 8 | 8 | 8 |
| 7 | 0.1 | 0.01 | 8 | 8 | 8 |
| 8 | 0.055 | 0.055 | 8 | 8 | 8 |
| 9 | 0.1 | 0.1 | 8 | 8 | 10 |
| 10 | 0.01 | 0.01 | 0 | 0 | 0 |
| 11 | 0.01 | 0.01 | 0 | 0 | 0 |
| 12 | 0.1 | 0.01 | 8 | 8 | 8 |
| 13 | 0.01 | 0.1 | 8 | 8 | 8 |
| 14 | 0.1 | 0.1 | 8 | 8 | 8 |
| 15 | 0.055 | 0.055 | 8 | 8 | 8 |

As a control individual components of the cell lysing agents Triton X100 and Guanidine Thiocyanate were separately used to coat ETF and the ZOI was tested as described above. The results showing the ZOI of ETF treated with Guanidine Thiocyanate or Triton X100 alone are shown in table 4 below.

TABLE 4

| Molar Concentration of cell lysing agent | Bacteria free areola in mm | | |
|---|---|---|---|
| 0.1M Guanidine | 0 | 0 | 0 |
| 0.1M Triton X100 | 0 | 0 | 0 |

The concentration of Guanidine Thiocyanate and Triton X100 that was taken up by the ETF paper was calculated using conductivity analysis. A calibration curve of concentration versus conductivity yielded an $R^2$ of 0.9945. Using the data from the conductivity experiment the concentration of guanidine present on the hybrid substrates was inferred.

A 7 mm punch of ETF paper was placed in a test tube and 20 mL of H2O was added. The solution was shaken for 5 minutes and left to stand, the conductivity meter was calibrated and the probe placed in the test tube, slightly agitated and the reading taken. The conductivity over the range of concentrations coated onto the ETF paper was analysed and the results are shown in Table 5 below and the results were plotted on a graph shown in FIG. 1.

TABLE 5

| Coating concentration Moles (guanidine thiocyanate on hybrid paper) | Conductivity mS |
|---|---|
| 0.1M | 0.928 |
| 0.2M | 1.541 |
| 0.3M | 1.917 |
| 0.4M | 2.573 |
| 0.5M | 2.802 |

Figure 2:
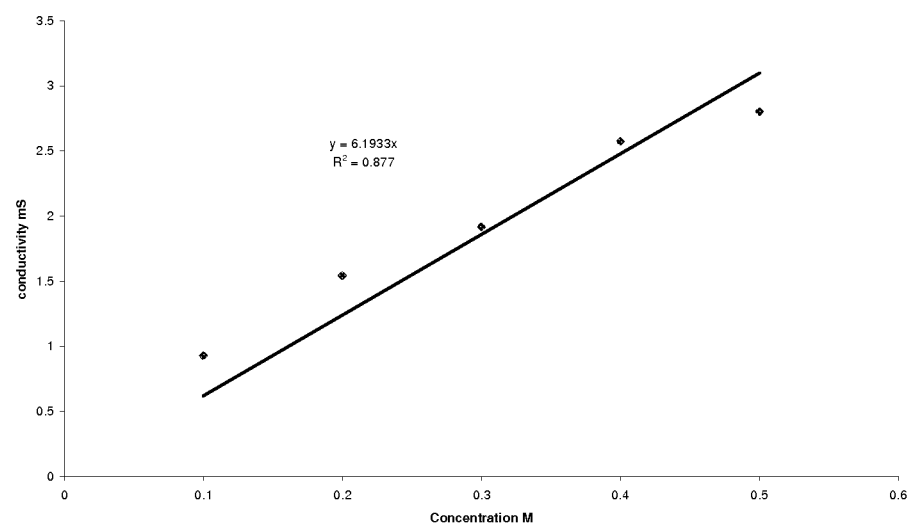
FIG. 2 shows the conductivity versus concentration of the guanidine thiocyanate and Triton X100 treated ETF paper.

The conductivity of ETF coated with Guanidine Thiocyanate and Triton X100 was determined and shown in FIG. 2. Using the established conductivity curve from the previous study an estimated coating concentration for guanidine on ETF was inferred and shown in table 6 below.

TABLE 6

| Coating concentration in Moles (guanidine on hybrid paper) | Actual concentration derived calculate using plot formula % W/V |
|---|---|
| 0.1M = 1.18% W/V | 0.030 |
| 0.2M = 2.36% W/V | 0.112 |
| 0.3M = 3.54% W/V | 0.161 |
| 0.4M = 4.72% W/V | 0.272 |
| 0.5M = 5.90% W/V | 0.279 |

Table 7 below represents the extracted data obtained from the conductivity analysis, the Triton X100 weight was calculated by subtracting the Theoretical Guanidine Thiocyanate weight on the ETF paper from the actual total weight increase of the Guanidine Thiocyanate and Triton 100X coated paper.

TABLE 7

| Coating concentration in Moles (guanidine on hybrid paper) | Actual concentration derived calculate using plot formula % W/V | Theoretical Guanidine weight present on each paper (g) | Weight increase in grams of the Guanidine:Triton X100 mixture | Triton X100 weight present on paper (g) |
|---|---|---|---|---|
| 0.1 | 0.030 | 0.020 | 0.1431 | 0.1231 |
| 0.2 | 0.112 | 0.027 | 0.1987 | 0.1717 |
| 0.3 | 0.161 | 0.045 | 0.3231 | 0.2781 |

TABLE 7-continued

| Coating concentration in Moles (guanidine on hybrid paper) | Actual concentration derived calculate using plot formula % W/V | Theoretical Guanidine weight present on each paper (g) | Weight increase in grams of the Guanidine:Triton X100 mixture | Triton X100 weight present on paper (g) |
|---|---|---|---|---|
| 0.4 | 0.272 | 0.061 | 0.4421 | 0.3811 |
| 0.5 | 0.279 | 0.066 | 0.4715 | 0.4055 |

While preferred illustrative embodiments of the present invention are described, one skilled in the art will appreciate that the present invention can be practiced by other than the described embodiments, which are presented for the purposes of illustration only and not by way of limitation. The present invention is limited only by the claims that follow.

What is claimed is:

1. A solid matrix for storing and/or lysing a biological sample comprising a surfactant and a chaotropic salt, wherein the concentration of the chaotropic salt to surfactant is 0.1M:0.1M, the surfactant is Triton X100, and the chaotropic salt is a guanidinium salt.

2. The solid matrix of claim 1, wherein the biological sample is selected from the group consisting of a cellular sample, blood, serum, semen, cerebral spinal fluid, synovial fluid, lymphatic fluid, saliva, buccal, cervical cell, vaginal cell, urine, faeces, hair, skin and muscle.

3. The solid matrix of claim 1, wherein the solid matrix is selected from the group consisting of alginate, glass, glass fiber, glass microfiber, silica, silica gel, silica oxide, cellulose, nitrocellulose, carboxymethylcellulose, polyester, polyamide, carbohydrate polymers, polypropylene, polytetrafluroethylene, polyvinylidinefluoride, wool and porous ceramics.

4. The solid matrix of claim 1, wherein the solid matrix is a cellulose based matrix.

5. The solid matrix of claim 4, additionally wherein said cellulose based matrix is in the form of a pre punched disc.

6. The solid matrix of claim 4, additionally wherein the cellulose based matrix is in the form of a pre punched disc.

7. A method of storing and/or lysing a biological sample comprising the steps:
    i) contacting a solid matrix of any preceding claim with a biological sample; and
    ii) storing said solid matrix with said biological sample, wherein the concentration of the chaotropic salt to surfactant is 0.1M:0.1M, the surfactant is Triton X100, and the chaotropic salt is a guanidinium salt.

8. The method of claim 7, further comprising a step iii) of recovering the cell lysate from the solid matrix.

9. The method of claim 7, wherein the biological sample is selected from a group consisting of a cellular sample, blood, serum, semen, cerebral spinal fluid, synovial fluid, lymphatic fluid, saliva, buccal, cervical cell, vaginal cell, urine, faeces, hair, skin and muscle.

10. A method of manufacturing a solid matrix comprising the steps:
    i) dipping a solid matrix into a mixture of a surfactant and a chaotropic salt wherein the concentration of said chaotropic salt to surfactant is 0.1M:0.1M, the surfactant is Triton X100, and the chaotropic salt is a guanidinium salt; and
    ii) allowing the solid matrix to dry.

11. The method of claim 10, wherein the solid matrix is selected from the group consisting of alginate, glass, glass fiber, glass microfiber, silica, silica gel, silica oxide, cellulose, nitrocellulose, carboxymethylcellulose, polyester, polyamide, carbohydrate polymers, polypropylene, polytetrafluroethylene, polyvinylidinefluoride, wool or porous ceramics.

12. A kit for storing and amplifying nucleic acid comprising the solid matrix of claim 1 and instructions for use thereof.

* * * * *